US012558069B2

(12) United States Patent
Li

(10) Patent No.: US 12,558,069 B2
(45) Date of Patent: Feb. 24, 2026

(54) METHODS AND DEVICES FOR DISPLAYING MEDICAL IMAGE

(71) Applicant: SHANGHAI UNITED IMAGING HEALTHCARE Co., LTD., Shanghai (CN)

(72) Inventor: Liu Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 608 days.

(21) Appl. No.: 17/953,007

(22) Filed: Sep. 26, 2022

(65) Prior Publication Data

US 2023/0094164 A1 Mar. 30, 2023

(30) Foreign Application Priority Data

Sep. 27, 2021 (CN) .......................... 202111137667.2

(51) Int. Cl.
A61B 8/00 (2006.01)
G06T 7/00 (2017.01)
(52) U.S. Cl.
CPC ............ A61B 8/483 (2013.01); G06T 7/0012 (2013.01); G06T 2207/10072 (2013.01)
(58) Field of Classification Search
CPC .................. A61B 8/483; G06T 7/0012; G06T 2207/10072
See application file for complete search history.

(56) References Cited

U.S. PATENT DOCUMENTS

| | | | | |
|---|---|---|---|---|
| 11,983,801 | B2 * | 5/2024 | Ishigaki .............. | G06F 3/04855 |
| 2008/0155451 | A1 | 6/2008 | Lundstrom et al. | |
| 2020/0121393 | A1 * | 4/2020 | Nakamura ........... | G06T 19/003 |
| 2021/0174938 | A1 | 6/2021 | Park et al. | |
| 2024/0428926 | A1 * | 12/2024 | Schreckenberg ....... | G06F 3/012 |

FOREIGN PATENT DOCUMENTS

| | | | | |
|---|---|---|---|---|
| CN | 101116110 A | 1/2008 | | |
| CN | 105608721 A | 5/2016 | | |
| CN | 106295405 A | 1/2017 | | |
| CN | 106683144 A | 5/2017 | | |
| CN | 106709930 A | 5/2017 | | |
| CN | 107194925 A | * | 9/2017 | ........... G06T 7/0012 |
| CN | 109544657 A | 3/2019 | | |

(Continued)

OTHER PUBLICATIONS

The First Office Action for Chinese Application No. 202111137667.2 dated Jul. 12, 2023 (6 pages).

(Continued)

*Primary Examiner* — Shefali D Goradia

(57) ABSTRACT

The present disclosure relates to the technical field of medical image visualization, and more particularly, to a method and a device for displaying a medical image, a computer apparatus, and a storage medium. The method includes: acquiring three-dimensional volume data; determining an initial layer corresponding to at least one dimensional direction from the three-dimensional volume data; receiving a viewing instruction for the three-dimensional volume data of a terminal; and determining and displaying a target layer based on the viewing instruction and each initial layer.

19 Claims, 4 Drawing Sheets

(a)      (b)      (a)      (b)

(56) References Cited

FOREIGN PATENT DOCUMENTS

| | | | | | |
|---|---|---|---|---|---|
| CN | 109767382 A | | 5/2019 | | |
| CN | 110599564 A | | 12/2019 | | |
| CN | 111192356 A | | 5/2020 | | |
| CN | 112330707 A | | 2/2021 | | |
| CN | 114266848 A | * | 4/2022 | ............. | G06T 11/00 |
| WO | WO-2019023909 A1 | * | 2/2019 | ........... | A61B 5/4244 |
| WO | WO2021146895 A1 | | 7/2021 | | |

OTHER PUBLICATIONS

Xue Junling: "Application of 3D visualization technology in computer tomography", Wireless Internet Technology, No. 4, Feb. 25, 2018 (Feb. 25, 2018).

Yang Liu et al: "Design and Development of the Multi2dimensional Ultrasonic Reconstruction and Visual ization System", Journal of Biomedical Engineering, No. 4, Aug. 25, 2009 (Aug. 25, 2009).

Cai Maorong et al: "Research and realization of medicine image 3D reconstruction system based on Java 3D", Microcomputer Information, No. 3, Jan. 30, 2007(Jan. 30, 2007).

European Search Report for European Application No. 22198128.5 dated Feb. 28, 2023 (9 pages).

Anonymous: "User Interface and Data Loading—3D Slicer Documentation", Jul. 25, 2021 (Jul. 25, 2021), pp. 1-15, XP93019307, 3D Slicer Documentation.

Andriy Fedorov et al: "3D Slicer as an image computing platform for the Quantitative Imaging Network", Magnetic Resonance Imaging, vol. 30, No. 9, Nov. 2012 (Nov. 2012), pp. 1323-1341, XP055572591, Tarrytown, NY, US.

Dong Kyun Jeong et al: "On-the-fly Generation of Multiplanar Reformation Images Independent of CT Scanner Type", Journal of Digital Imaging; the Journal of the Society for Computer Applications in Radiology, Springer-Verlag, NE, vol. 21, No. 3, Mar. 24, 2007 (Mar. 24, 2007), pp. 306-311, XP019596193.

* cited by examiner

S202

Acquire three-dimensional volume data.

S204

Determine an initial layer corresponding to at least one dimensional direction from the three-dimensional volume data.

S206

Receive a viewing instruction for the three-dimensional volume data of a terminal.

S208

Determine and display a target layer based on the viewing instruction and each initial layer.

(a)                                        (b)

(a)          (b)

(a)          (b)

~100

Acquisition Module

~200

Initial Layer
Determination Module

~300

Viewing Instruction
Receiving Module

~400

Target Layer
Determination And
Display Module

Processor

System Bus

Operating System

Internal Memory

Computer Program

Network
Interface

Data Base

Non-transitory Storage
Medium

Computer Apparatus

METHODS AND DEVICES FOR DISPLAYING MEDICAL IMAGE

CROSS-REFERENCES TO RELATED APPLICATIONS

The present application claims priority to Chinese Patent Application No. 202111137667.2, entitled "METHODS AND DEVICE FOR DISPLAYING MEDICAL IMAGE, COMPUTER APPARATUS, AND STORAGE MEDIUMS", filed on Sep. 27, 2021, which is incorporated by reference herein for all purposes.

TECHNICAL FIELD

The present disclosure relates to the technical field of medical image visualization, and more particularly, to a method and a device for displaying a medical image, a computer apparatus, and a storage medium.

BACKGROUND

Multi-planar reconstruction (MPR) refers to stacking two-dimensional medical images and creating three-dimensional volume data, and then performing reconstruction and display of images in sagittal plane, coronal plane, and other arbitrary planes. In general, in order to better observe the lesion of a patient, physicians mostly observe an MPR plane image of a patient, and further observe the lesion on the MPR plane image to obtain a final analysis and detection result.

In the conventional methods, when performing display and interaction of the MPR planar image, only the conventional continuous display or discrete display can be provided, while the consistency and flexibility of the display and the interaction cannot be ensured.

SUMMARY

Based on the above, it is necessary to provide a method and a device for displaying a medical image, a computer apparatus, and a storage medium that can ensure the flexibility of the display and the consistency of the interaction of the medical image.

A method for displaying a medical image is provided. The method includes:

acquiring three-dimensional volume data;

determining an initial layer corresponding to at least one dimensional direction from the three-dimensional volume data;

receiving a viewing instruction for the three-dimensional volume data of a terminal; and determining and displaying a target layer based on the viewing instruction and each initial layer.

In an embodiment, the determining the initial layer corresponding to the at least one dimensional direction from the three-dimensional volume data includes:

determining the initial layer corresponding to the at least one dimensional direction based on a dimension size of image data in the at least one dimensional direction.

In an embodiment, the above method further includes:

receiving a mode selection instruction sent by the terminal, the mode selection instruction involving a viewing mode of the target layer.

The determining and displaying the target layer includes:

determining and displaying the target layer according to the viewing mode.

In an embodiment, the viewing mode includes a continuous mode and a discrete mode.

In an embodiment, the determining and displaying the target layer based on the viewing instruction and each initial layer includes:

determining a center layer position and a layer thickness range corresponding to the at least one dimensional direction according to the viewing instruction; and determining the target layer based on the center layer position and the layer thickness range, and displaying the target layer.

In an embodiment, the viewing instruction is a page-turning instruction or a drag instruction, and the determining and displaying the target layer based on the viewing instruction and each initial layer includes:

determining the target layer based on the position of the initial layer in at least one dimension and the page-turning instruction, and displaying the target layer; and determining the target layer based on the position of the initial layer in at least one dimension and the dragging instruction, and displaying the target layer.

In an embodiment, the viewing instruction is a display layer thickness modification instruction, and the determining and displaying the target layer based on the viewing instruction and each initial layer includes:

determining a display layer thickness based on the display layer thickness modification instruction, and determining and displaying the target layer based on the display layer thickness and a viewing mode.

A device for displaying a medical image is also provided. The device includes:

an acquisition module, configured to acquire three-dimensional volume data;

an initial layer determination module, configured to determine an initial layer corresponding to at least one dimensional direction from the three-dimensional volume data;

a viewing instruction receiving module, configured to receive a viewing instruction for the three-dimensional volume data of a terminal; and a target layer determination and display module, configured to determine and display a target layer based on the viewing instruction and each initial layer.

A computer apparatus is further provided. The computer apparatus includes a memory that stores a computer program, and a processor that, when executing the computer program, performs the steps of any one of the above embodiments.

A computer readable storage medium is further provided. The computer readable storage medium stores a computer program which, when executed by a processor, performs the steps of the method of any one of the above embodiments.

In the above method and device for displaying a medical image, the computer apparatus, and the storage medium, the three-dimensional volume data is acquired, the initial layer corresponding to at least one dimensional direction is determined from the three-dimensional volume data, the viewing instruction for the three-dimensional volume data of the terminal is received, and then the target layer is determined and displayed based on the viewing instruction and each initial layer. Therefore, the initial layer can be determined from the three-dimensional volume data, and then the target layer can be determined according to the viewing instruction and the initial layer, so that the target layer displayed is adapted to the viewing instruction, and different displays can be performed based on different modes, thereby improving the consistency and flexibility of the interaction and the display.

DETAILED DESCRIPTION OF THE EMBODIMENTS

To make the purposes, technical solutions and advantages of the present disclosure to be more apparent and understandable, reference will be made to the accompanying drawings and embodiments to describe the present disclosure in detail below. It should be understood that the specific embodiments described herein are only used to explain the present disclosure and not intended to limit the present disclosure.

Figure 1:
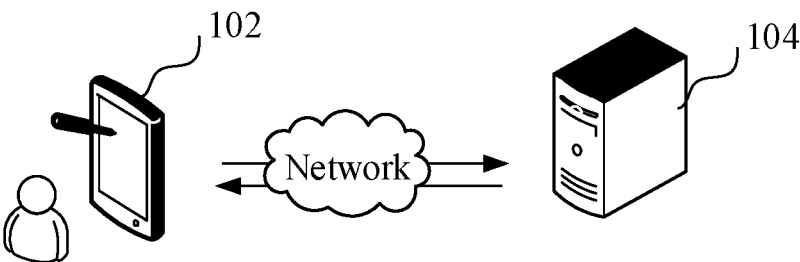
FIG. 1 is a diagram illustrating an application scenario of a method for displaying a medical image in an embodiment.

The method for displaying a medical image provided by the present disclosure may be applied to the application environment as shown in FIG. 1. A terminal 102 communicates with a server 104 via a network. A user may use the terminal 102 to scan and detect an object to be detected, and generate three-dimensional volume data. After obtaining the three-dimensional volume data, the server 104 may determine an initial layer corresponding to at least one layer from the three-dimensional volume data. Further, the server 104 may receive a viewing instruction for the three-dimensional volume data of the terminal 102, and determine and display a target layer based on the viewing instruction and each initial layer. The terminal 102 may be, but is not limited to, various medical image acquisition devices, such as computed tomography (CT), magnetic resonance (MR), positron emission computed tomography (PET), and the like, and the server 104 may be implemented by a separate server or a server cluster composed of multiple servers.

Figure 2:
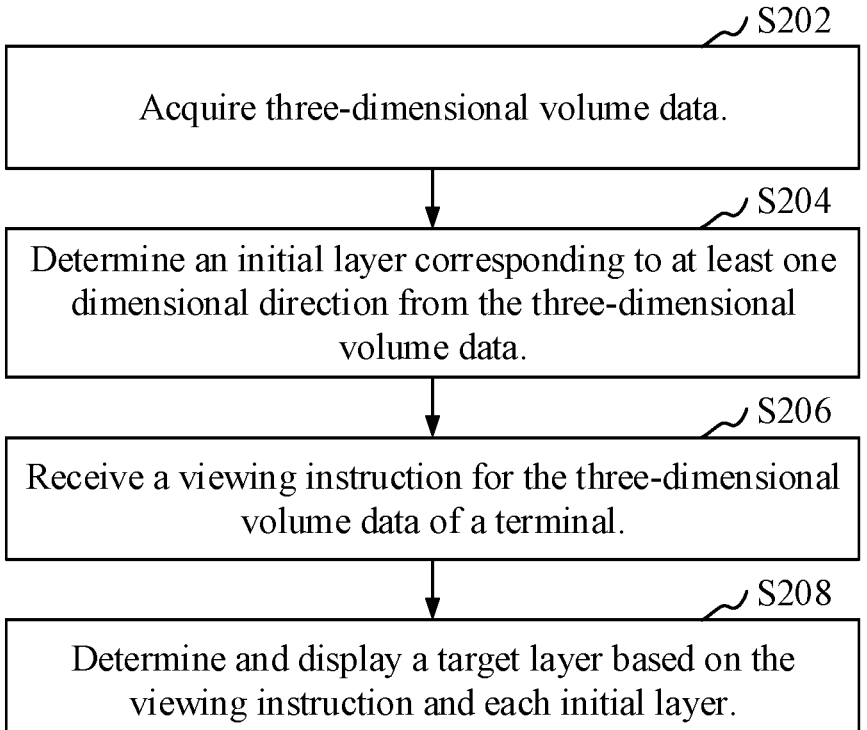
FIG. 2 is a schematic flow diagram illustrating a method for displaying a medical image in an embodiment.

In an embodiment, as shown in FIG. 2, a method for displaying a medical image is provided. Taking the method applied to the server in FIG. 1 as an example for illustration, the method includes the following steps.

In step S202, three-dimensional volume data is acquired.

Figure 3:
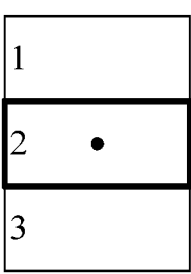
FIG. 3 is a schematic diagram illustrating an original image sequence in an embodiment.

The three-dimensional volume data refers to three-dimensional data generated after performing scanning and acquisition on an object to be detected by various medical image acquisition devices. The three-dimensional volume data may include image data in at least one dimensional direction. For example, the image data may be in a dimension such as sagittal and/or coronal and/or transverse. The image data in each of the dimensions is arranged in sequence, and as shown in FIG. 3, the image data in a certain dimension may be arranged in sequence.

In step S204, an initial layer corresponding to at least one dimensional direction is determined from the three-dimensional volume data.

The initial layer is a plane image of the MPR image in any one dimensional direction, such as a plane image corresponding to one of different dimensional directions such as sagittal, coronal, and transverse.

In this embodiment, the initial layer is different depending on the application scenario. For example, when the display of the MPR image is performed for the first time, the initial layer refers to a layer to be displayed by default based on the three-dimensional volume data. In another scenario, such as a display for the second time, the initial layer may be a target layer previously displayed, positioned and stored. For example, in the previous display, the layer thickness is changed and the target layer is viewed and stored, and at the time of the display for the second time, the initial layer may be the target layer loaded based on the layer thickness at the time of the previous display.

In this embodiment, the server may determine whether it is a display for the first time or a display for the second time based on the acquired three-dimensional volume data, determine the initial layer based on different scenarios, and display the initial layer.

In step S206, a viewing instruction for the three-dimensional volume data of a terminal is received.

The viewing instruction refers to an instruction sent by the user through the terminal to view the three-dimensional volume data, and may include a page-turning instruction, a dragging instruction, a display layer thickness modification instruction, and the like.

In the present embodiment, the terminal may generate, based on an operation on the terminal by the user, a viewing instruction corresponding to the operation, and send the viewing instruction to the server so that the server may receive the corresponding instruction.

In step S208, a target layer is determined and displayed based on the viewing instruction and each initial layer.

In this embodiment, the server may determine and display a corresponding target layer based on different instruction contents according to the viewing instruction.

The target layer is a target layer to be displayed in the MPR image, for example, a layer image corresponding to different dimensional directions such as sagittal, coronal, and transverse, respectively.

In this embodiment, the server may determine the target layer in at least one dimensional direction in the MPR image, and display the corresponding target layer, that is, display the MPR image.

In the above method for displaying the medical image, the three-dimensional volume data is acquired, the initial layer corresponding to at least one dimensional direction is determined from the three-dimensional volume data, the viewing instruction for the three-dimensional volume data of the terminal is received, and then the target layer is determined and displayed based on the viewing instruction and each initial layer. Therefore, the initial layer can be determined from the three-dimensional volume data, and then the target layer can be determined according to the viewing instruction and the initial layer, so that the target layer displayed is adapted to the viewing instruction, and different displays can be performed based on different modes, thereby improving the consistency and flexibility of the interaction and the display.

In an embodiment, determining the initial layer corresponding to the at least one dimensional direction from the three-dimensional volume data may include: determining the initial layer corresponding to the at least one dimensional direction based on a dimension size of image data in the at least one dimensional direction.

The dimension size may refer to the size of the data quantity (or the size of the volume data), or the number of layers in a certain dimension.

As described above, the method for determining the initial layer may be different based on different application scenarios. For example, the initial layer may be determined based on the dimension size of the image data when the display is performed for the first time, and the initial layer may be determined based on the layer thickness stored and the target layer determined in the previous display when the loading is performed for the second time.

In the present embodiment, for the display for the first time, after obtaining the three-dimensional volume data, the server may analyze the image data in each dimension, determine the dimension size of the image data in each dimension, and determine the initial layer based on the dimension size.

In an embodiment, the server may determine the initial layer according to the number of layers of the image data in each dimension.

Specifically, the server may make a parity determination on the number of layers of the image data, and determine the initial layer based on the parity of the number of layers and the definition of the initial layer.

Figure 4:
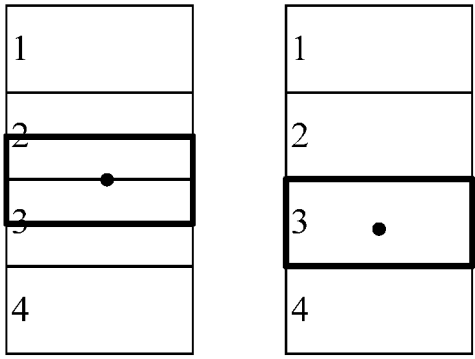
FIG. 4 is a schematic diagram illustrating an original image sequence in another embodiment.

For example, the server may define the initial layer as a central layer. When the number of layers of the image data is an odd number, the server may determine the layer located in the middle position as the initial layer, and display the initial layer. When the number of layers of the image data is an even number, the server may determine the initial layer from the two layers located in the middle position. For example, referring to FIG. 3, the image data includes three layers, which are labeled from top to bottom as layer 1, layer 2, and layer 3, respectively, then the server may determine the middle layer, that is, layer 2, as the corresponding initial layer. Referring to FIG. 4, the image data includes four layers, which are labeled from top to bottom as layer 1, layer 2, layer 3 and layer 4, respectively, then the server may determine that the layers corresponding to the middle position are layer 2 and layer 3, and then randomly determine a layer from layer 2 and layer 3 as the initial layer.

In the above embodiment, by acquiring the number of layers of the image data, and then determining the initial layer in different ways according to the number of layers, the corresponding initial layer can be obtained according to a uniform standard for different scenarios, and the display effect can be improved.

In an embodiment, the above method may further include: receiving a mode selection instruction sent by the terminal, the mode selection instruction involving a viewing mode of the target layer.

The mode selection instruction is configured to indicate a viewing mode or interactive mode in which the display and the interaction is performed, and which may include, but is not limited to, a continuous mode or a discrete mode.

In this embodiment, when the user performs interaction and viewing on the three-dimensional volume data based on the terminal, the user can select the viewing mode by triggering the viewing mode selection control on the interface of the terminal, and send the corresponding mode selection instruction generated to the server, so that the server can perform subsequent processing according to the corresponding viewing mode selection instruction.

In this embodiment, determining and displaying the target layer may include: determining and displaying the target layer according to the viewing mode.

Specifically, the server determines the viewing mode selected by the user based on the mode selection instruction, and displays the target layer according to the selected viewing mode when performing a viewing display.

In this embodiment, as previously described, the three-dimensional volume data includes image data in at least one dimension, and the image data of each dimension includes a plurality of layers. When the server performs the viewing display based on the viewing instruction of the terminal, a target layer in the at least one dimension is displayed.

In this embodiment, the effect of the display may be different depending on the viewing mode.

Figure 5:
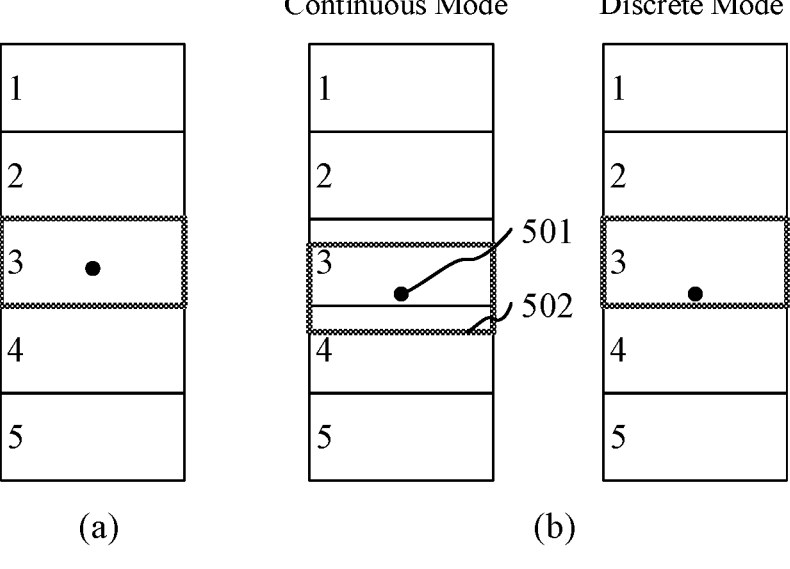
FIG. 5 is a schematic diagram illustrating a method for determining a target layer in an embodiment.

Specifically, when the viewing mode is the continuous mode, the server may continuously performing the viewing display of the image data based on the viewing instruction, as shown in the continuous mode in (b) of FIG. 5, and the displayed target layer may be partial data corresponding to a plurality of layers in the three-dimensional volume data, such as partial data of layer 3 and partial data of layer 4. 501 is the display center, and 502 is the display range. When the viewing mode is the discrete mode, the displayed layer is a layer completely consistent with a layer in the three-dimensional volume data. As shown in the discrete mode in (b) of FIG. 5, the display center is not in the middle position of the display range, and the display range completely corresponds to a layer in the three-dimensional volume data.

In the foregoing embodiment, by receiving the viewing mode selection instruction sent by the terminal, and then performing viewing and interaction according to the viewing mode corresponding to the viewing mode selection instruction, the user can select different viewing modes according to the viewing needs to perform the viewing display, thereby improving the user experience.

As described above, the viewing instruction may include a page-turning instruction, a dragging instruction, and a display layer thickness modification instruction. Based on different viewing instructions, the determined target layer may be different, and the display effect may be different.

In an embodiment, the viewing instruction is a page-turning instruction or a dragging instruction.

The page-turning instruction refers to an instruction for performing page-turning display according to a specified dimension, for example, performing page-turning display in one dimensional direction of sagittal, coronal, or transverse in the three-dimensional volume data.

The dragging instruction refers to an instruction for dragging the center layer position of the display center to any position of the three-dimensional volume data in any one dimensional direction and performing an indiscriminate display.

In this embodiment, determining and displaying the target layer based on the viewing instruction and each initial layer may include: determining a target layer based on the page-turning instruction and a position of the initial layer in at least one dimension, and displaying the target layer; and determining the target layer based on a drag instruction and the position of the initial layer in at least one dimension, and displaying the target layer.

In this embodiment, the user can perform the page-turning display through the terminal, so that the page-turning display can be performed in a layer-by-layer manner according to the layer having a determined layer thickness in the three-dimensional volume data.

Similarly, when the viewing instruction is a dragging instruction, the user can perform dragging display through the terminal, and can drag the display center in the three-dimensional volume data, determine the target layer, and display the target layer.

In this embodiment, depending on the viewing mode, the target layer displayed may be different in the dragging display and the page-turning display. For example, with continued reference to FIG. 5, in the continuous mode, when the dragging display is performed, as the display center is dragged, the target layer is a layer corresponding to the display range, such as the corresponding layer 3 and layer 4, or an integer layer closest to the display center. In the discrete mode, as the display center is dragged, the display range always corresponds to an initial layer (2D layer) in which the display center is located in the three-dimensional volume data. That is, the initial layer in which the display center is located is layer 4, then the display range corresponds to layer 4, and the target layer is layer 4. When the display center is dragged from layer 4 to layer 5, the display range is switched to layer 5, and layer 5 is displayed.

In an embodiment, the viewing instruction is a display layer thickness modification instruction.

The layer thickness refers to the thickness of the display range (that is, the thickness of a rendering layer), and the layer thickness modification instruction may include information on the modified thickness of the display range.

In this embodiment, determining and displaying the target layer based on the viewing instruction and each initial layer may include: determining a display layer thickness based on the display layer thickness modification instruction, and determining and displaying the target layer based on the display layer thickness and the viewing mode.

Figure 6:
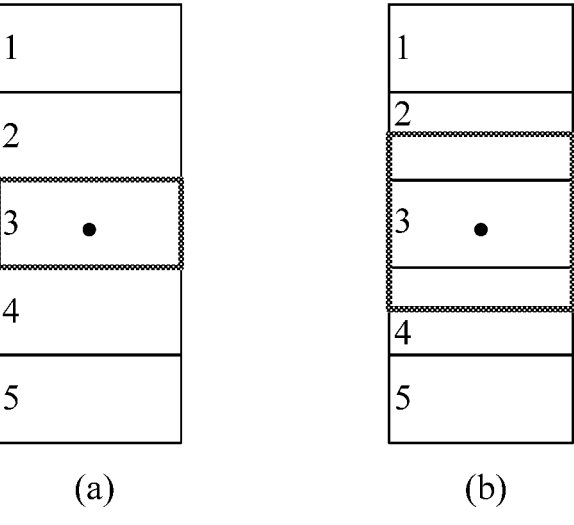
FIG. 6 is a schematic diagram illustrating a method for determining a target layer in another embodiment.

Specifically, as shown in (a) of FIG. 6, the initial layer thickness of the display range determined by the server may be consistent with the layer thickness of the layer in each dimension in the three-dimensional volume data.

In this embodiment, the server may modify the layer thickness of the display range based on the display layer thickness modification instruction, for example, modify the layer thickness of the display range to correspond to the double of the initial layer thickness, as shown in (b) of FIG. 6.

In this embodiment, after the server performs the modification of the display layer thickness based on the layer thickness modification instruction, the server may determine the target layer according to the modified display range, and perform the display.

Figure 7:
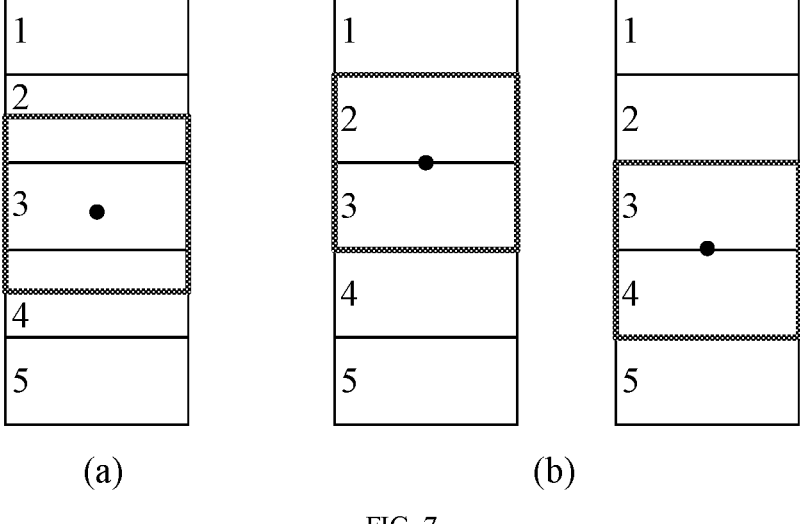
FIG. 7 is a schematic diagram illustrating a method for determining a target layer in yet another embodiment.

Referring to FIG. 7, and taking the display range being the double of the layer thickness as an example, in the continuous mode, as shown in (a) of FIG. 7, the displayed data may be all or part of the data including the layer 2, the layer 3, and the layer 4 within the display range in the three-dimensional volume data, while in the continuous mode, as shown in (b) of FIG. 7, the displayed data is the data of two consecutive layers within the displayed range in the three-dimensional volume data, such as the layer 3 and the layer 4, or the layer 2 and the layer 3.

In an embodiment, the determining and displaying the target layer based on the viewing instruction and each initial layer may include: determining a center layer position and a layer thickness range corresponding to at least one dimensional direction based on the viewing instruction; and determining a target layer based on the center layer position and the layer thickness range, and displaying the target layer.

The center layer position refers to the position of the layer corresponding to the display center described above. The thickness range refers to the range of the display area.

In this embodiment, the server may determine the center layer position and the layer thickness range corresponding to at least one dimensional direction, such as double of the layer thickness, based on the viewing instruction, such as the display layer thickness modification instruction, the page-turning instruction, the dragging instruction, or the like as described above, and performs the display.

In this embodiment, the server may perform viewing display of the MPR image according to the center layer position and the layer thickness range in combination with the viewing mode. For example, when in the continuous mode, data of a plurality of layers that the display layer thickness spans may be correspondingly displayed, and when the viewing mode is the discrete mode, data of complete initial layers corresponding to the display layer thickness may be displayed.

It should be understood that although the steps in the flow diagram of FIG. 2 are sequentially displayed as indicated by the arrows, these steps are not necessarily performed in the order indicated by the arrows. Unless explicitly stated herein, the performing order of the steps is not be limited strictly, and the steps may be performed in other orders. Moreover, at least part of the steps in FIG. 2 may include a plurality of sub-steps or phases, which are not necessary to be performed simultaneously, but may be performed at different times, and for the performing order thereof, it is not necessary to be performed sequentially, but may be performed by turns or alternately with other steps or sub-steps of other steps or at least part of the phases.

Figures 8, 9:
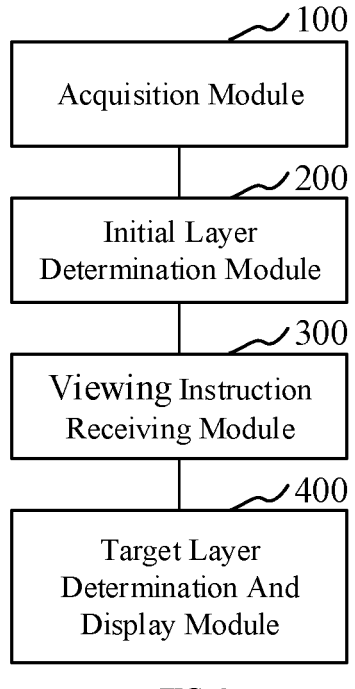
FIG. 8 is a block diagram illustrating a configuration of a device for displaying a medical image in an embodiment.
FIG. 9 is a diagram illustrating an internal configuration of a computer apparatus in one embodiment.

In an embodiment, as shown in FIG. 8, there is provided a device for displaying a medical image, and the device includes: an acquisition module 100, an initial layer determination module 200, a viewing instruction receiving module 300, and a target layer determination and display module 400.

The acquisition module 100 is configured to acquire three-dimensional volume data.

The initial layer determination module 200 is configured to determine an initial layer corresponding to at least one dimensional direction from the three-dimensional volume data.

The viewing instruction receiving module 300 is configured to receive a viewing instruction for the three-dimensional volume data of a terminal.

The target layer determination and display module 400 is configured to determine and display a target layer based on the viewing instruction and each initial layer.

In an embodiment, the initial layer determination module 200 is configured to determine an initial layer in a corresponding dimensional direction based on a dimension size of the image data in at least one dimensional direction.

In an embodiment, the above device may further includes:

a mode selection instruction receiving module, configured to receive a mode selection instruction sent by the terminal, the mode selection instruction involving a viewing mode of the target layer.

In the present embodiment, the target layer determination and display module 400 is configured to determine and display the target layer according to the viewing mode.

In an embodiment, the viewing mode may include a continuous mode and a discrete mode.

In an embodiment, the target layer determination and display module 400 may include:

a position and layer thickness determination submodule, configured to determine a center layer position and a layer thickness range corresponding to at least one dimensional direction according to the viewing instruction; and a target layer determination and display submodule, configured to determine a target layer based on the center layer position and the layer thickness range, and display the target layer.

In an embodiment, the viewing instruction is a sliding instruction or a dragging instruction.

In this embodiment, the target layer determination and display module 400 may include:

a first target layer determination and display submodule, configured to determine a target layer based on the position of the initial layer in at least one dimension and the page-turning instruction, and display the target layer; and a second target layer determination and display submodule, configured to determine a target layer based on the position of the initial layer in at least one dimension and the dragging instruction, and display the target layer.

In an embodiment, the viewing instruction is a display layer thickness modification instruction.

In this embodiment, the target layer determination and display module 400 is configured to determine the display layer thickness based on the display layer thickness modification instruction, and determine and display the target layer based on the display layer thickness and the viewing mode.

For the specific limitation of the device for displaying the medical image, reference may be made to the above limitation on the method for displaying the medical image, which will not be repeated here. Each of the above modules in the device for displaying the medical image may be implemented in whole or in part by software, hardware and combinations thereof. Each of the above modules may be embedded in or independent of a processor in a computer apparatus in hardware forms, or may be stored in the memory of the computer apparatus in software forms, so that the processor can invoke and execute the operations corresponding to each of the above modules.

In an embodiment, a computer apparatus is provided. The computer apparatus may be a server, and have an internal configuration as shown in FIG. 9. The computer apparatus includes a processor, a memory, a network interface, and a database connected by a system bus. The processor of the computer apparatus is configured to provide computing and control capabilities. The memory of the computer apparatus includes a non-transitory storage medium and an internal memory. The non-volatile storage medium stores an operating system, computer programs and a data base. The internal memory provides a running environment for the operating system and the computer program in the non-transitory storage medium. The database of the computer apparatus is configured to store data such as the original image sequence, the interactive instruction, and the target layer. The network interface of the computer apparatus is configured to communicate with an external terminal via a network connection. The computer program is executed by the processor to implement the method for displaying the medical image.

It will be understood by those skilled in the art that the configuration shown in the block diagram FIG. 9 is only a part of the configuration related to the solution of the present disclosure, and does not constitute a limitation of the computer apparatus to which the solution of the present disclosure is applied. The specific computer apparatus may include more or fewer components than those shown in the figure, or combine some components, or have different component arrangements.

In an embodiment, there is provided a computer apparatus, the computer apparatus includes a memory that stores a computer program, and a processor that, when executing the computer program, performs the steps of: acquiring three-dimensional volume data; determining an initial layer corresponding to at least one dimensional direction from the three-dimensional volume data; receiving a viewing instruction for the three-dimensional volume data of a terminal; and determining and displaying a target layer based on the viewing instruction and each initial layer.

In an embodiment, the determining the initial layer corresponding to the at least one dimensional direction from the three-dimensional volume data implemented by the processor when executing the computer program may include: determining the initial layer corresponding to the at least one dimensional direction based on a dimension size of the image data in the at least one dimensional direction.

In an embodiment, the processor, when executing the computer program, may further perform the step of: receiving a mode selection instruction sent by the terminal, the mode selection instruction involving a viewing mode of the target layer.

In this embodiment, the determining and displaying the target layer implemented by the processor when executing the computer program may include: determining and displaying the target layer according to the viewing mode.

In an embodiment, the viewing mode may include a continuous mode and a discrete mode.

In an embodiment, the determining and displaying the target layer based on the viewing instruction and each initial layer implemented by the processor when executing the computer program may include: determining a center layer position and a layer thickness range corresponding to at least one dimensional direction based on the viewing instruction; and determining the target layer based on the center layer position and the layer thickness range, and displaying the target layer.

In an embodiment, the viewing instruction is a page-turning instruction or a dragging instruction.

In the present embodiment, the determining and displaying the target layer based on the viewing instruction and each initial layer implemented by the processor when executing the computer program may include: determining the target layer based on the page-turning instruction and a position of the initial layer in at least one dimension, and displaying the target layer; and determining the target layer based on a drag instruction and the position of the initial layer in at least one dimension, and displaying the target layer.

In an embodiment, the viewing instruction is a display layer thickness modification instruction.

In the present embodiment, the determining and displaying a target layer based on the viewing instruction and each initial layer implemented by the processor when executing the computer program may include: determining a display layer thickness based on the display layer thickness modification instruction, and determining and displaying the target layer based on the display layer thickness and the viewing mode.

In an embodiment, there is provided a computer readable storage medium on which a computer program is stored.

When the computer program is executed by a processor, the following steps are performing: acquiring three-dimensional volume data; determining an initial layer corresponding to at least one dimensional direction from the three-dimensional volume data; receiving a viewing instruction for the three-dimensional volume data of a terminal; and determining and displaying a target layer based on the viewing instruction and each initial layer.

In an embodiment, the determining the initial layer corresponding to the at least one dimensional direction from the three-dimensional volume data implemented when the computer program is executed by the processor may include: determining the initial layer corresponding to the at least one dimensional direction based on a dimension size of the image data in the at least one dimensional direction.

In an embodiment, the computer program, when executed by the processor, may further perform the step of: receiving a mode selection instruction sent by the terminal, the mode selection instruction involving a viewing mode of the target layer.

In the present embodiment, the determining and displaying the target layer implemented when the computer program is executed by the processor may include: determining and displaying the target layer according to the viewing mode.

In an embodiment, the viewing mode may include a continuous mode and a discrete mode.

In an embodiment, the determining and displaying the target layer based on the viewing instruction and each initial layer implemented when the computer program is executed by the processor may include: determining a center layer position and a layer thickness range corresponding to at least one dimensional direction based on the viewing instruction; and determining the target layer based on the center layer position and the layer thickness range, and displaying the target layer.

In an embodiment, the viewing instruction is a page-turning instruction or a dragging instruction.

In this embodiment, determining and displaying the target layer based on the viewing instruction and each initial layer implemented when the computer program is executed by the processor may include: determining the target layer based on the page-turning instruction and a position of the initial layer in at least one dimension, and displaying the target layer; and determining the target layer based on a drag instruction and a position of the initial layer in at least one dimension, and displaying the target layer.

In an embodiment, the viewing instruction is a display layer thickness modification instruction.

In this embodiment, the determining and displaying the target layer based on the viewing instruction and each initial layer implemented when the computer program is executed by the processor may include: determining a display layer thickness based on the display layer thickness modification instruction, and determining and displaying the target layer based on the display layer thickness and the viewing mode.

Those of ordinary skill in the art may understand that all or part of the processes in the method of the above embodiments may be completed by instructing relevant hardware by the computer program, and the computer program may be stored in a non-transitory computer readable storage medium. When the computer program is executed, the processes of the above methods in the embodiments may be included. Any reference to the memory, the storage, the database or other medium used in various embodiments provided in the present disclosure may include a non-transitory memory and/or a transitory memory. The non-transitory memory may include a read only memory (ROM), a programmable ROM (PROM), an electrically programmable ROM (EPROM), an electrically erasable programmable ROM (EEPROM) or a flash memory. The transitory memory may include a random access memory (RAM) or an external cache memory. As illustration rather than limitation, the RAM is available in a variety of forms, such as a static RAM (SRAM), a dynamic RAM (DRAM), a synchronous DRAM (SDRAM), a dual data rate SDRAM (DDRS-DRAM), an enhanced SDRAM (ESDRAM), a synchlink DRAM (SLDRAM), a rambus direct RAM (RDRAM), a direct rambus dynamic RAM (DRDRAM), a rambus dynamic RAM (RDRAM), and the like.

The technical features of the above embodiments can be combined arbitrarily. To simplify the description, not all possible combinations of the technical features in the above embodiments are described. However, all of the combinations of these technical features should be considered as within the scope of this disclosure, as long as such combinations do not contradict with each other.

The above describe embodiments merely represent several embodiments of the present disclosure, and the description thereof is more specific and detailed, but it should not be construed as limiting the scope of the present disclosure. It should be noted that, several modifications and improvements may be made for those of ordinary skill in the art without departing from the concept of the present disclosure, and these are all within the protection scope of the present disclosure. Therefore, the protection scope of the present disclosure shall be subject to the appended claims.

What is claimed is:

1. A method for displaying a medical image, the method comprising:

acquiring three-dimensional volume data;

determining an initial layer corresponding to at least one dimensional direction from the three-dimensional volume data;

receiving a viewing instruction for the three-dimensional volume data of a terminal; and determining and displaying a target layer based on the viewing instruction for the three-dimensional volume data and each initial layer, wherein the determining and displaying the target layer based on the viewing instruction for the three-dimensional volume data and each initial layer comprises:

determining a center layer position and a layer thickness range corresponding to the at least one dimensional direction according to the viewing instruction; and determining the target layer based on the center layer position and the layer thickness range, and displaying the target layer.

2. The method according to claim 1, wherein the determining the initial layer corresponding to the at least one dimensional direction from the three-dimensional volume data comprises:

determining the initial layer corresponding to the at least one dimensional direction based on a dimension size of image data in the at least one dimensional direction.

3. The method according to claim 2, wherein the determining the initial layer corresponding to the at least one dimensional direction from the three-dimensional volume data comprises:

determining a parity of the number of layers of the image data; and determining the initial layer corresponding to the at least one dimensional direction based on the parity of the number of layers of the image data and a predetermined rule for the initial layer.

4. The method according to claim 1, wherein the determining the initial layer corresponding to the at least one dimensional direction from the three-dimensional volume data comprises:

determining the initial layer corresponding to the at least one dimensional direction based on a dimension size of image data in the at least one dimensional direction when display is performed for a first time; and determining the initial layer corresponding to the at least one dimensional direction based on a layer thickness stored and the target layer determined in a previous display when the display is performed for a second time.

5. The method according to claim 1, further comprising:

receiving a mode selection instruction sent by the terminal, the mode selection instruction involving a viewing mode of the target layer, wherein the determining and displaying the target layer comprises:

determining and displaying the target layer according to the viewing mode.

6. The method according to claim 5, wherein the viewing mode comprises a continuous mode and a discrete mode.

7. The method according to claim 6, further comprising:

performing display of the image data based on the viewing instruction continuously when the viewing mode is the continuous mode; and displaying a layer completely consistent with an integer layer in which a display center is located in the three-dimensional volume data when the viewing mode is the discrete mode.

8. The method according to claim 1, wherein the viewing instruction is a page-turning instruction, a drag instruction, or a display layer thickness modification instruction.

9. The method according to claim 8, wherein the determining and displaying the target layer based on the viewing instruction and each initial layer comprises:

determining the target layer based on a position of the initial layer in at least one dimension and the page-turning instruction, and displaying the target layer; and determining the target layer based on the position of the initial layer in at least one dimension and the dragging instruction, and displaying the target layer.

10. The method according to claim 8, wherein the determining and displaying the target layer based on the viewing instruction and each initial layer comprises:

determining a display layer thickness based on the display layer thickness modification instruction, and determining and displaying the target layer based on the display layer thickness and a viewing mode.

11. A computer apparatus comprising a processor and a memory storing a computer program, wherein a method for displaying a medical image is implemented when the processor executes the computer program, and the method comprises:

acquiring three-dimensional volume data;

determining an initial layer corresponding to at least one dimensional direction from the three-dimensional volume data;

receiving a viewing instruction for the three-dimensional volume data of a terminal; and determining and displaying a target layer based on the viewing instruction for the three-dimensional volume data and each initial layer, wherein the determining and displaying the target layer based on the viewing instruction for the three-dimensional volume data and each initial layer comprises:

determining a center layer position and a layer thickness range corresponding to the at least one dimensional direction according to the viewing instruction; and determining the target layer based on the center layer position and the layer thickness range, and displaying the target layer.

12. The computer apparatus according to claim 11, wherein the determining the initial layer corresponding to the at least one dimensional direction from the three-dimensional volume data comprises:

determining the initial layer corresponding to the at least one dimensional direction based on a dimension size of image data in the at least one dimensional direction.

13. The computer apparatus according to claim 12, wherein the determining the initial layer corresponding to the at least one dimensional direction from the three-dimensional volume data comprises:

determining a parity of the number of layers of the image data; and determining the initial layer corresponding to the at least one dimensional direction based on the parity of the number of layers of the image data and a predetermined rule for the initial layer.

14. The computer apparatus according to claim 11, wherein the determining the initial layer corresponding to the at least one dimensional direction from the three-dimensional volume data comprises:

determining the initial layer corresponding to the at least one dimensional direction based on a dimension size of image data in the at least one dimensional direction when display is performed for a first time; and determining the initial layer corresponding to the at least one dimensional direction based on a layer thickness stored and the target layer determined in a previous display when the display is performed for a second time.

15. The computer apparatus according to claim 11, wherein the method implemented when the processor executes the computer program further comprises:

receiving a mode selection instruction sent by the terminal, the mode selection instruction involving a viewing mode of the target layer; and wherein the determining and displaying the target layer comprises:

determining and displaying the target layer according to the viewing mode.

16. The computer apparatus according to claim 11, wherein the viewing mode comprises a continuous mode and a discrete mode, and the method implemented when the processor executes the computer program further comprises:

performing display of the image data based on the viewing instruction continuously when the viewing mode is the continuous mode; and displaying a layer completely consistent with an integer layer in which a display center is located in the three-dimensional volume data when the viewing mode is the discrete mode.

17. The computer apparatus according to claim 11, wherein the determining and displaying the target layer based on the viewing instruction and each initial layer comprises:

determining a center layer position and a layer thickness range corresponding to the at least one dimensional direction according to the viewing instruction; and determining the target layer based on the center layer position and the layer thickness range, and displaying the target layer.

18. The computer apparatus according to claim 11, wherein the viewing instruction is a page-turning instruction or a drag instruction, and the determining and displaying the target layer based on the viewing instruction and each initial layer comprises:

determining the target layer based on a position of the initial layer in at least one dimension and the page-turning instruction, and displaying the target layer; and determining the target layer based on the position of the initial layer in at least one dimension and the dragging instruction, and displaying the target layer.

19. A non-transitory computer readable storage medium on which a computer program is stored, wherein a method for displaying a medical image is implemented when the computer program is executed by the processor, and the method comprises:

acquiring three-dimensional volume data;

determining an initial layer corresponding to at least one dimensional direction from the three-dimensional volume data;

receiving a viewing instruction for the three-dimensional volume data of a terminal; and determining and displaying a target layer based on the viewing instruction for the three-dimensional volume data and each initial layer, wherein the determining and displaying the target layer based on the viewing instruction for the three-dimensional volume data and each initial layer comprises:

determining a center layer position and a layer thickness range corresponding to the at least one dimensional direction according to the viewing instruction; and determining the target layer based on the center layer position and the layer thickness range, and displaying the target layer.

* * * * *